United States Patent [19]

Barker et al.

[11] Patent Number: 5,153,330
[45] Date of Patent: Oct. 6, 1992

[54] THIAPENTANAMIDE DERIVATIVES

[75] Inventors: John M. Barker; Patrick R. Huddleston, both of Nottingham, England

[73] Assignee: Shell Internationale Research Maatschappij, B.V., Netherlands

[21] Appl. No.: 751,575

[22] Filed: Aug. 22, 1991

Related U.S. Application Data

[63] Continuation of Ser. No. 566,330, Aug. 10, 1990, abandoned, which is a continuation of Ser. No. 205,646, Jun. 13, 1988, abandoned.

[30] Foreign Application Priority Data

Jul. 7, 1987 [GB] United Kingdom ............... 8715925

[51] Int. Cl.⁵ ........................................ C07D 333/38
[52] U.S. Cl. ..................................................... 549/61
[58] Field of Search ........................................ 549/61

[56] References Cited

PUBLICATIONS

Wagner & Zook Synthetic Organic Chem. (1953) pp. 596, 597.
Gronowitz, S., Thiophene and its Derivatives, vol. 1, pp. 120-121 (John Wiley & Sons, 1985).
Pirner, H., "Uber Umsetzungen von, α,β-Dihalogencarbon Saureestern mit α-Mercaptocarbonylverbindungen", Dissertation, Friedrich Alexander Universitat, Erlangen-Nurnberg, 1985.

Huddleston, P. R., and Barker, John M., Synthetic Communications, 9(8), 731-734 (1979).

*Primary Examiner*—Alan Siegel

[57] ABSTRACT

A compound of the general formula

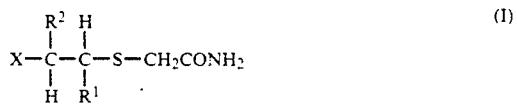

(I)

in which X represents a chlorine or bromine atom, $R^1$ represents a hydrogen atom, a C(1-6) alkyl group, a benzyl group or a phenyl group optionally substituted by a C(1-6) alkyl group, and $R^2$ represents the group CN or the group COOR$^3$ in which $R^3$ represents a C(1-6) alkyl group, a process for the preparation of a compound of formula (I), and the use of a compound of formula (I) in the preparation of a compound of the general formula.

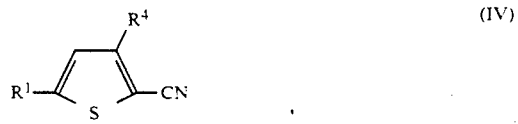

(IV)

in which $R^1$ is as defined above and $R^4$ represents an amino group or a hydroxyl group.

1 Claim, No Drawings

THIAPENTANAMIDE DERIVATIVES

This application is a continuation, of application Ser. No. 07/566,330, filed Aug. 10, 1990 now abandoned, which is a continuation of Ser. No. 07/205,646, filed Jun. 13, 1988, now abandoned.

The present invention relates to a process for the preparation of certain 2-cyanothiophene derivatives, to certain thiapentanamide derivatives of use as intermediates in the process, and to a process for the preparation of the thiapentanamides.

2-Cyanothiophene derivatives are of interest as intermediates in the synthesis of agrochemicals, pharmaceuticals and other products, see, for example, British patent application number GB 2122619; Rossy et al, J. Org Chem, 45 (4) pages 617 to 620; and Acta. Chem. Scand. Ser B., 1975, vol B29, part 2, pages 224 to 232. However, they are often difficult to synthesize.

A process for the preparation of several 2-cyanothiophene derivatives is described in "Thiophene and its Derivatives, Volume 1" by S Gronowitz (John Wiley and Sons, 1985), p121. The process starts from acetylmercaptoacetonitrile and comprises only one step. However, acetylmercaptoacetonitrile is not a readily available starting material. Furthermore, the yield of 2-cyanothiophene is in some cases very poor. For example, 3-amino-2-cyanothiophene is obtained in only 25 to 30% yield.

Surprisingly it has now been found that certain 2-cyanothiophene derivatives may advantageously be prepared in a multi-step process using certain thiapentanamide derivatives.

According to one aspect of the invention, there is provided a compound of the general formula

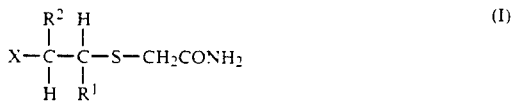

in which X represents a chlorine or bromine atom, $R^1$ represents a hydrogen atom, a C(1-6) alkyl group, a benzyl group or a phenyl group optionally substituted by a C(1-6) alkyl group, and $R^2$ represents the group CN or the group $COOR^3$ in which $R^3$ represents a C(1-6) alkyl group.

Preferably $R^1$ represents a hydrogen atom.

Preferably $R^2$ represents the group CN or a methoxycarbonyl group. More preferably $R^2$ represents the group CN.

According to another aspect of the invention, there is provided a process for the preparation of a compound of formula (I) as defined above which comprises reacting the compound of formula $$HSCH_2CONH_2 \quad (II)$$

with a compound of the general formula $$HR^1C=CXR^2 \quad (III)$$

in which X, $R^1$ and $R^2$ are as defined above, in the presence of a base.

The process is conveniently effected in the presence of an aprotic organic solvent such as an ether, e.g. tetrahydrofuran or dioxan; an ester, e.g. ethyl acetate; a nitrile; e.g. acetonitrile; a substituted amide, e.g. dimethylformamide or dimethylacetamide; a haloalkane, e.g. dichloromethane; a ketone, e.g. acetone; an aromatic hydrocarbon, e.g. benzene or toluene; a sulphoxide, e.g. dimethyl sulphoxide, or a tertiary amine, e.g. triethylamine or pyridine.

Suitable bases for the reaction include weak bases such as alkali metal carbonates, e.g. sodium carbonate or potassium carbonate; and tertiary amines, e.g. triethylamine or pyridine. It will be appreciated that when the base is a tertiary amine, it may act as both a base and a solvent.

The process is conveniently effected at a temperature in the range of from $-10°$ to $100°$ C., preferably from $-5°$ to $25°$ C.

The compound of formula (II) is cheap to produce, and is readily available.

The compounds of the general formula (I) are useful in the preparation of 3-amino-2-cyanothiophene, 3-hydroxy-2-cyanothiophene and certain derivatives thereof.

Accordingly, the invention further provides the use of a compound of the general formula (I) as defined above in the preparation of a compound of the general formula

in which $R^1$ is as defined above and $R^4$ represents an amino group or a hydroxyl group.

The compounds of formula (IV) may be prepared from the compounds of formula (I) in a two step process which comprises the step of dehydration of an amide group to afford a nitrile group followed by the step of cyclisation to afford a thiophene ring.

Accordingly, the invention also provides a process for the preparation of a compound of formula (IV) as defined above, which comprises dehydrating a compound of the general formula

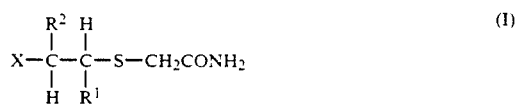

where X, $R^1$ and $R^2$ are as defined above, by reaction with a dehydrating agent to afford a compound of the general formula

where X, $R^1$ and $R^2$ are as defined above, and then cyclising the compound of the general formula (V) by treatment with a base.

The step of dehydration is conveniently effected using a conventional dehydrating agent such as phosphorus pentoxide; a phosphorus oxyhalide such as phosphorus oxychloride; a phosphorus halide such as phosphorus pentachloride; a sulphonyl halide such as p-toluenesulphonyl chloride; or thionyl chloride.

The step of dehydration may conveniently be effected in the presence of an organic solvent such as an ether, e.g. tetrahydrofuran or dioxan; an ester, e.g. ethyl acetate; a nitrile; e.g. acetonitrile; a substituted amide, e.g. dimethylformamide or dimethylacetamide; a haloalkane, e.g. dichloromethane; an aromatic hydrocarbon, e.g. benzene or toluene; a sulphoxide, e.g. dimethylsulphoxide, or a tertiary amine, e.g. pyridine.

Preferably the step of dehydration is effected in the presence of pyridine by reaction with p-toluenesulphonyl chloride followed by treatment with an acid such as hydrochloric acid.

The temperature may conveniently be in the range of from 0° to 125° C., preferably from 15° to 75° C.

The step of cyclisation is conveniently effected in the presence of an inert organic solvent such as an ether, e.g. tetrahydrofuran or dioxan; an alcohol, e.g. methanol or ethanol; an amide, e.g. dimethylformamide or dimethylacetamide; a sulphoxide, e.g. dimethylsulphoxide; or an aromatic hydrocarbon e.g. benzene or toluene.

Conveniently the step of cyclisation is effected at a temperature in the range of from $-10°$ to $15°$ C., preferably from 0° to 10° C.

The base employed in the step of cyclisation may be a strong base such as an alkali metal hydroxide, e.g. potassium hydroxide or sodium hydroxide, which may be anhydrous or in the form of a concentrated aqueous solution; an alkali metal alkoxide, e.g., sodium methoxide or potassium ethoxide; or an alkali metal hydride, e.g. sodium hydride.

Conveniently, the product of the reaction of a compound of formula (II) with a compound of formula (III) may be used directly to prepare a compound of formula (V) without isolation of a compound of formula (I).

The following examples illustrate the invention Examples 1,4 and 7 illustrate the preparation of compounds of formula (I). Examples 2,3,5,6 and 8 illustrate the use of compounds of formula (I) in the preparation of compounds of formula (IV).

EXAMPLE 1

5-Chloro-5-cyano-3-thiapentanamide

A solution of 2-mercaptoacetamide (20 g) in dry pyridine (80 ml) was stirred whilst 2-chloroacrylonitrile (18 ml) was added slowly with ice-bath cooling. After the addition was complete, the ice-bath was removed, and the mixture was stirred for 45 minutes. The resultant mixture contained the title compound. A portion of the mixture was shaken repeatedly with petroleum ether (b.p. 60° to 80° C.) to leave the title compound as a syrup. $^1$H nmr $\delta$ (CD$_3$COCD$_3$) 5.50 (1H,t,J=7HZ, CH$_2$CH), 3.40 (2H, d,J=7HZ, CH$_2$CH), 3.50(2H, s, CH$_2$CN).

EXAMPLE 2

1-Chloro-1,4-dicyano-3-thiabutane

To the mixture obtained from Example 1, tosyl chloride (42 g) was added in portions with cooling. The resultant mixture was stirred for 5.5 hours, and then stood overnight. The solution was then poured into 4M hydrochloric acid (300 ml), stirred for 30 minutes, and then extracted with dichloromethane (×4). The combined extracts were washed with saturated brine, dried (magnesium sulphate) and evaporated to obtain the title compound as a dark red oil (30.95 g) $^1$H n.m.r. $\delta$ (CDCl$_3$) 3.35(2H, d, J=7Hz, CH$_2$CH), 3.55(2H,s,CH$_2$CN), 4.77 (1H,t, J=7Hz, CH$_2$CH).

EXAMPLE 3

3-Amino-2-cyanothiophene

A solution of 1-chloro-1,4-dicyano-3-thiabutane (8.66 g) in dichloromethane (40 ml) was stirred in an ice-bath whilst 40% sodium hydroxide (6.5 ml) was added in two portions, keeping the temperature below 10° C. The mixture was stirred for 4.25 hours, then saturated brine (40 ml) was added. The organic layer was separated, dried (magnesium sulphate), and evaporated to obtain the title compound as a red oil (4.71 g), $^1$H n.m.r. $\delta$ (CDCl$_3$) 4.73 (2H, br s, NH$_2$), 6.52 (1H,d,J=5Hz, 4-H), 7.25 (1H, d, J=5Hz, 5-H).

The overall yield of 3-amino-2-cyanothiophene (starting from 2-mercaptoacetamide and 2-chloroacrylonitrile) was thus 61%, which is clearly superior to the yield of 25–30% reported by Gronowitz.

EXAMPLE 4

5-Chloro-5-methoxycarbonyl-3-thiapentanamide

2-Mercaptoacetamide (18.79 g) was stirred in a mixture of dry 1,4-dioxan (200 ml) and dry pyridine (33.5 ml)) whilst methyl 2-chloroacrylate (24.88 g) was added dropwise over 15 minutes. The mixture was stirred for 1 hour then stood overnight. The resultant mixture contained the title compound.

EXAMPLE 5

5-Chloro-5-methoxycarbonyl-3-thiapentanenitrile

To the mixture obtained from Example 4, tosyl chloride (39.34 g) was added in portions with vigorous stirring and heat was evolved. The mixture was stirred for 9.5 hours, stood overnight, then poured into water (500 ml), and extracted with dichloromethane. The combined extracts were washed with water (×2) and saturated brine, dried (magnesium sulphate) and evaporated to yield the title compound as a dark red oil (27.05 g).

EXAMPLE 6

5-Chloro-5-methoxycarbonyl-3-thiapentanenitrile

Tosyl chloride (18.82 g) was added in portions to a stirred solution of 5-chloro-5-methoxycarbonyl-3-thiapentanamide (19 g), in dry pyridine (95 ml). Heat was evolved during the addition. The mixture was stirred for 4 hours, stood overnight, and poured into 4M hydrochloric acid (400 ml) and extracted with dichloromethane. The combined extracts were washed with 4M hydrochloric acid (×3) and saturated brine, dried (magnesium sulphate) and evaporated to obtain the title compound as a dark red oil (14.2 g) $^1$H n.m.r. $\delta$ (CDCl$_3$) 3.28 (2H,d, J=7Hz, CH$_2$CH), 3.45 (2H, s, CH$_2$CN), 3.83 (3H,s,CO$_2$Me), 4.54 (1H,t, J=7Hz, CH$_2$CH).

EXAMPLE 7

5-Chloro-5-methoxycarbonyl-3-thiapentanamide

2-Mercaptoacetamide (10.0 g) and methyl 2-chloroacrylate (13.24 g) were dissolved in warm acetone (100 ml), and potassium carbonate (7.58 g) was added in one portion. Heat was evolved. The mixture was heated to reflux for 2 hours. The red solution was filtered hot using a filter aid, and the residue washed with hot acetone (×2). The filtrate and washings were combined and evaporated to obtain the title compound as a red oil (19.92 g) $^1$H n.m.r. $\delta$ (CDCl$_3$/DMSO-d$_6$) 3.05–3.18 (4H, overlapping s and d. CH₂COR and CH₂CH) 3.76 (3H,s,CO₂Me), 4.67 (1H,t, J=7Hz, CHCH₂), 6.92 (1H, br s, CONH), 7.43 (1H, br s, CONH).

EXAMPLE 8

2-cyano-3-hydroxy thiophene

A solution of 5-chloro-5-methoxycarbonyl-3-thiapentanenitrile (5 g) in dry methanol (20 ml) was stirred at room temperature whilst 25% sodium methoxide in methanol (11.75 ml, 2.1 equivalents) was added dropwise over 2 minutes. A sharp rise in temperature was noted. The mixture was stirred for 2.5 hours at ambient temperature then poured into water (250 ml), and washed with ether (×3). The washings were discarded. The aqueous fraction was cooled, acidified with concentrated hydrochloric acid and extracted with ether (×4). The combined extracts were washed with water, dried (magnesium sulphate), and evaporated to obtain the title compound as a red, waxy solid (2.74 g). ¹H n.m.r. δ (CDCl₃/DMSO-d₆) 6.70 (1H, d, J=5Hz, 4-H), 7.43 (1H, d, J=5Hz), 8.77 (1H, br s, OH).

We claim:

1. A process for the preparation of a compound of the formula:

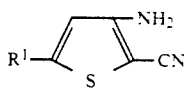  (IV)

in which R¹ represents a hydrogen atoms, a C₁₋₆ alkyl group, a benzyl group or a phenyl group optionally substituted by a C₁₋₆ alkyl group,
which process comprises reacting in the presence of a base a compound of formula:

HSCH₂CONH₂  (II)

with a compound of the formula:

HR¹C=CXCN  (III)

in which X represents a chlorine or bromine atom, and R¹ is as defined above, to yield a compound of the formula:

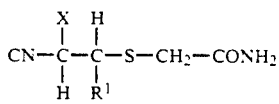  (I)

in which X, and R¹ are as defined above,
dehydrating said compound of the formula (I) by reaction with a dehydrating agent to yield a compound of the general formula:

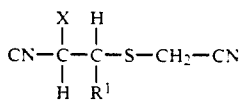  (V)

in which X, and R¹ are as defined above,
followed by cyclising said compound of the formula (V) by treatment with a base to yield said compound of formula (IV).

* * * * *